US006300443B1

(12) United States Patent
Solomon et al.

(10) Patent No.: US 6,300,443 B1
(45) Date of Patent: Oct. 9, 2001

(54) PROCESS FOR PREPARING POLYMERIC MICROGELS

(75) Inventors: David Henry Solomon, Officer; Simmi Abrol, Wheelers Hill; Peter Agapitos Kambouris, Kew; Mark Graham Looney, Brunswick, all of (AU)

(73) Assignee: The University of Melbourne, Victoria (AU)

( * ) Notice: Subject to any disclaimer, the term of this patent is extended or adjusted under 35 U.S.C. 154(b) by 0 days.

(21) Appl. No.: 09/341,583

(22) PCT Filed: Jan. 15, 1998

(86) PCT No.: PCT/AU98/00015

§ 371 Date: Sep. 7, 1999

§ 102(e) Date: Sep. 7, 1999

(87) PCT Pub. No.: WO98/31739

PCT Pub. Date: Jul. 23, 1998

(30) Foreign Application Priority Data

Jan. 15, 1997 (AU) .................................................. PO4607

(51) Int. Cl.[7] .................................................... C08F 2/00
(52) U.S. Cl. ........................ 526/220; 526/217; 526/328; 526/335; 526/336; 526/341; 526/346
(58) Field of Search ..................................... 526/217, 220, 526/328, 335, 336, 341, 346

(56) References Cited

U.S. PATENT DOCUMENTS

| 4,414,357 | 11/1983 | Wright et al. . |
| 4,424,331 | 1/1984 | Gruber . |
| 4,539,348 | 9/1985 | Gajria et al. . |
| 4,666,962 | 5/1987 | Ravichandran et al. . |

FOREIGN PATENT DOCUMENTS

| 0114478 A1 | 8/1984 | (EP) . |
| 0228565 A2 | 7/1987 | (EP) . |
| 2159161 A | 11/1985 | (GB) . |
| WO96/10044 A1 | 4/1996 | (WO) . |

Primary Examiner—Helen L. Pezzuto
(74) Attorney, Agent, or Firm—Alston & Bird LLP

(57) ABSTRACT

A process for preparation of a microgel comprising reacting an alkoxyamine with an unsaturated monomer composition comprising a cross-linking agent comprising at least two double bonds and optionally one or more further monomers selected from monounsaturated monomers and conjugated diene monomers.

19 Claims, No Drawings

PROCESS FOR PREPARING POLYMERIC MICROGELS

The present invention relates to a process for the preparation of microgels and to a composition for use in such a process.

Microgels are macromolecules which possess a combination of very high molecular weight and a solubility and viscosity similar to linear or branched polymers of relatively low molecular weight. Microgels are an intermediate structure between conventional linear or branched polymers such as polyethylene or polycarbonate and networks such as vulcanised natural rubber. The dimensions of microgels are compatible with high molecular weight linear polymers but their internal structure resembles a network.

The properties of microgels make them particularly useful in a wide range of applications such as in additives, in advanced material formulations for foams or fibres, in coating compositions, binders and redispersible latexes. Microgels may also be used to improve the ease of processing and to improve the structural strength and dimensional stability of the final products. A further potential use for microgels is as additives for high impact polymers. Microgels embedded in a matrix of conventional linear polymer may act to stabilise the whole structure by distributing mechanical tension. Microgels are also useful in biological systems and as pharmaceutical carriers.

A number of methods have been used for the preparation of microgels, however these methods generally have a number of serious deficiencies. For example, extreme care is required in preparing microgels as the multiple double bonds present within these systems may readily undergo intermolecular reactions which can lead to intractable networks. Other procedures such as those described by OKay,O. and Funke,W. in *MACROMOLECULES*, 1990, 23 at 2623–2628 require high purity solvent and reagents as well as an inert atmosphere and are complicated by undesirable side reactions. Despite the unique properties of microgels the difficulties in preparing them have limited their potential and commercial use.

According to the present invention we provide a process for preparation of a microgel comprising reacting an alkoxyamine with an unsaturated monomer composition comprising a cross-linking agent comprising at least two double bonds and optionally one or more further monomer selected from mono-unsaturated monomers and conjugated dienes.

In a particularly preferred aspect the invention provides a process for the preparation of a microgel polymer including the free radical polymerization of a composition including:

an alkoxyamine comprising an oligomer containing an aminoxy substituent; and a cross-linking agent comprising at least two double bonds.

The microgel prepared by this aspect of the invention generally has linear arms which are linked via the cross-linking agent to provide a core in the form of a cross-linked network. This type of microgel may conveniently be referred to as a star microgel.

Throughout the description and claims of this specification, the word "comprise" and variations of the word, such as "comprising" and "comprises", is not intended to exclude other additives or components or integers.

The process of the invention may be carried out using various additives such as solvent, promoters or radical species. In some instances the efficiency of the process may be improved by the addition of nitroxide radical species such as TEMPO (tetramethyl-1-oxyl radical) or other nitroxide radical which is hereinafter described. It is believed that the nitroxide radical enables the molecular weight distribution to be controlled and provides rate enhancement in many cases. The use of nitroxide radicals in the process of the invention is particularly preferred when, in the alkoxy amine of Formula I n is zero or less than about 5. Radical initiators such as AIBN may also be used to provide rate enhancement.

The alkoxyamine used in the present invention is preferably of Formula I

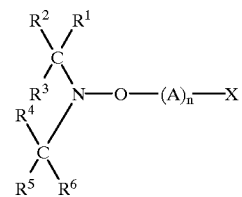

(I)

wherein —(A)$_n$X is a radical species capable of polymerising in the presence of the monomer component comprising the cross-linking agent. In the initiators of formula (I) the groups R$^1$, R$^2$, R$^5$ and R$^6$ are the same or different straight chain or branched substituted or unsubstituted alkyl groups of a chain length sufficient to provide steric hindrance and weakening of the O—(A)$_n$X bond, and R$^3$ and R$^4$ are the same or different straight chain or branched alkyl or substituted alkyl groups or R$^3$CNCR$^4$ may be part of a cyclic structure which may have fused with it another saturated or aromatic ring. Mixtures of alkoxyamines may be used if desired.

In the group (A)$_n$X the unit A is a monomer unit which, when there is more than one A, may be the same or different;

n is zero or greater than zero; and

X is an initiator fragment residue.

The proportion of components used in the process of the invention will generally depend on the desired properties of the microgel and the intended application. Generally the microgel is prepared using up to 60 mole percent of cross-linking agent based on moles of polymerizable components. More preferably the cross-linking agent will comprise up to 50 mole % of the total of the polymerizable components. Typically the alkoxyamine will compose from about 5 to about 95 mole % of the polymerizable components.

The present invention allows a higher proportion of cross-linking agent than has previously been possible for microgel compositions. Prior art microgels have generally been restricted to using no more than several mole percent of cross-linking agent. The ability to use high concentrations of cross-linking agent enables microgels to be prepared with a high density conferring significant advantages in rheology control. Accordingly it is preferred that the process of the invention use at least 5 mole percent of cross-linking agent based on total of the polymerizable components and most preferably from 10 to 50%.

In the process of the invention when the alkoxyamine contains from zero to 5 monomeric units (ie. n is from 0 to 5) then it is particularly preferred that the monomer composition include a further monomer such as a mono-unsaturated monomer or conjugated diene monomer. As the number of monomer units decreases the improvement provided by using a mono-unsaturated monomer increases. When n is 0 or 1 a further monomer is typically used.

Typically when the number of monomeric units is less than 5 the mono-unsaturated monomer will be present in up to 80 mole % based on the total number of moles of polymerizable components and more preferably from 10 to 80%. In this embodiment the alkoxyamine is typically present in an amount of at least 5 mole % and preferably in an amount of from 5 to 60%.

When preparing star microgels it is preferred that the number of monomeric units (A) in the alkoxyamine is at least 3 and more preferably at least 5. In this embodiment the alkoxyamine will typically comprise from 50 to 95 mole % of the total polymerizable component and the mono-unsaturated monomer may comprise from 0 to 45 mole %.

The one or more further monomers when used in the process of the invention, may be any well known monounsaturated monomer such as an alkene, acrylate, methacrylate, styrene or styrenic monomer, acrylonitrile or substituted acrylonitrile, or a conjugated diene monomer such as butadiene, isoprene, chloroprene, cyclopentadiene vinyl acetate, vinylidene chloride and polyvinylidene dichloride.

The properties of the microgel and its reactivity in subsequent applications may be controlled by the choice of monomers and their functional groups. Examples of monomers include $C_1$ to $C_{10}$ alkenes, alkylacrylates, alkylmethacrylates, hydroxyalkylacrylates, hydroxyalkylmethacylates, haloalkylacrylates, haloalkylmethacrylates. alkoxyalkylacrylates, alkoxyalkylmeth acrylates, optionally mono N-substituted or di-N-substituted aminoalkylmethacrylates, cycloalkylaerylates, cycloalkylmethacrylates, phenoxyacrylate, phenoxymethacylate, alkylene glycolacrylate, alkylene glycol methacrylate, polyalkyleneglycolacrylate, polyalkyleneglycolmethacrylate, acrylamides, methacrylamides, derivatives of acrylamides and methacylamides, esters of fumaric acid, maleic acid and maleic acid anhydride and esters of maleic acid, N-vinyl carbazole, N-vinylpyrrolidone, vinyl pyridine, benzyl acrylate and benzyl methacrylate.

In the alkoxyamine of Formula I suitable groups for $R^1$, $R^2$, $R^5$ and $R^6$ are methyl, ethyl, propyl, butyl, isopropyl, isobutyl, t-butyl, neopentyl, benzyl or the like.

Suitable groups for $R^3$ and/or $R^4$ are methyl, ethyl, propyl, butyl, isopropyl, isobutyl, t-butyl, pentyl, octadecyl or the like, of if $R^3CNCR^4$ is part of a cyclic structure this cyclic structure may be

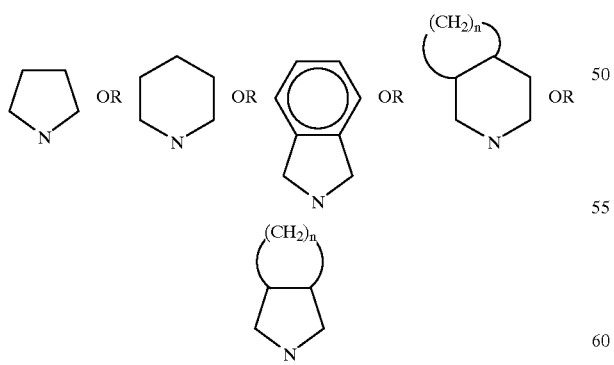

The cyclic structure may be substituted.

For controlled free radical polymerization by the initiators of Formula I it is desirable that the nitroxide radical of Formula II does not initiate any substantial free radical polymerization of the unsaturated monomers itself.

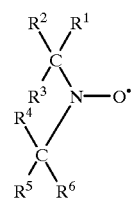

(II)

The weakening of the O—X bond is generally achieved at moderate temperatures to provide free radical polymerization.

Specific examples of suitable nitroxides include the following:

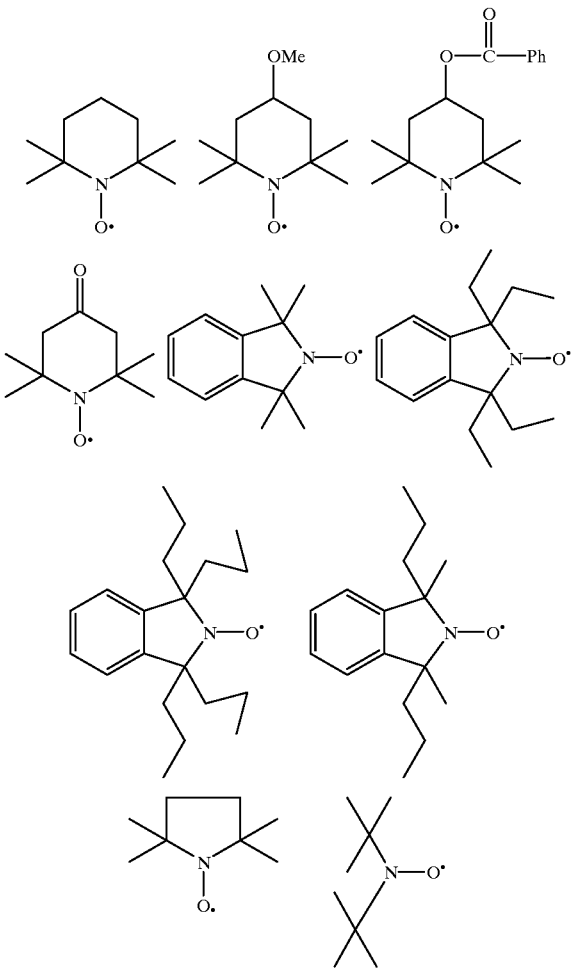

Examples of the initiator fragment residue include radicals of formula:

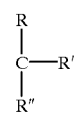

wherein R, R' and R", are independently selected from the group consisting of hydrogen, alkyl, phenyl, cyano, carboxcylic acid, carboxcylic groups and substituted groups thereof and wherein two of R, R' and R" may together form an aliphatic or aromatic ring.

Alkoxy amines such as those of Formula I can be manufactured by heating a nitroxide radical of Formula II in the presence of a stoichiometric amount of a carbon centred free radical X, where X may be generated by any of the methods well known in the art e.g. by the decomposition of an azo compound, by scission of an alkoxy radical or by H atom abstraction from a suitable monomeric or polymeric compound or by addition of a free radical to an olefin. More specifically X can be generated by the thermal or photochemical dissociation of X-X, or X-Z-X or X-Z-Z-X where Z is a group which in its uncombined form is a small stable molecule e.g. $CO_2$ or $N_2$.

The alkoxyamine so formed may be isolated and purified for later use or it may be used without further purification for the initiation of polymerization.

The nitroxides of Fomula II may be readily prepared by the oxidation of the appropriate secondary amine or hydroxylamine, reduction of the appropriate nitro or nitroso compound, or by the addition of free radicals to nitrones. Alternatively the alkoxyamine initiators can either by prepared or generated in situ by the addition of a source of free radicals to a suitable nitroxide either in the presence of an unsaturated monomer or with the monomer being added after the free radicals have reacted with the nitroxide.

In the preferred embodiment of the invention which provides a star microgel the group —$(A)_n$X is an oligomer preferably of at least 3 monomer units but typically having at least 5 monomer units (ie. n≧5). The molecular weight of the oligomer group $(A)_n$ is preferably at least 1000.

The oligomer may be a homopolymer or a copolymer. When the oligomer is a copolymer it may be a statistical or a block copolymer. The monomers used in preparing the oligomer may include one or more functional groups in addition to the double bond. These additional functional groups may be selected to confer the desired polarity or reactivity on the arms of the star type microgel. Examples of additional functional groups include halo, amino, hydroxy, carboxyl, mercapto, substituted amino, silane groups and epoxy. Hydroxy functional groups such as in the monomer hydroxyethyl methacrylate are particularly preferred. A monomer which includes the additional functional group or groups may form a homopolymer or a comonomer of a statistical or block copolymer.

When —$(A)_n$X is an oligomer the oligomer may be prepared by any suitable method known in the art. In many instances it is preferred to use the nitroxide radical to prepare the oligomer from monomer units. For example an oligomer may be derived from monomer A by insertion of further monomer units between nitroxide radical of Formula II and the monomer.

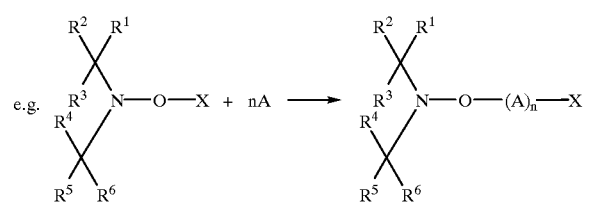

by a reversible termination process. The process is called controlled-growth free radical polymerization in the present specification.

Statistical copolymers may be prepared by using a mixture of monomers and block copolymers may be prepared by changing the monomer.

Details of such nitroxide mediated polymerization process are provided in U.S. Pat. No. 4,581,429 (Solomon et al). Such an oligomer may be prepared using the monounsaturated monomers and butadiene monomers listed above.

An aminoxy capped oligomer may also be prepared by anionic polymerization. For example oligomers derived from anionic polymerization such as poly(styryllithium) may be reacted with a pryridinium salt such as 1-oxo-4-methoxy-2,2,6,6-tetramethylpyridinium salt (OAS) to provide the corresponding nitroxyl radical (MTEMPO). An example of such a procedure is described by Yoshida et al in the paper "Synthesis of Polystyrene having an Aminoxy Terminal by the Reactions of Living Polystyrene with Oxoaminium Salt and with Corresponding Nitroxyl Radical", *Macromolecules* 27 (12) 3119–3124. Alternatively an oligomer may be prepared by anionic polymerization and the oligomer anion reacted with AIBN which may subsequently be substituted with a nitroxide. The preparation of AIBN terminated oligomers following anionic polymerization is described by Vinchon et al "Preparation de Promoteurs Azoiques Macromoleculaires Par Voie Anionique. *European Polymer Journal*, 12 pp. 317–321. This paper prepares a block copolymer of styrene and methylmethacralate and a copolymer of styrene and vinyl chloride which may be utilised in the process of the present invention.

Preferably the oligomer used in the present invention will have a molecular weight of at least 1000 and more preferably from 3000 to 15000. The nitrosyl radical portion of Formula I may, for example, be provided by PROPOXYL (2,2,5,5-tetramethyl-1-pyrrolidinyloxy) and derivatives thereof, TEMPO (2,2,6,6-tetramethyl-1-piperidinylopcy) and derivatives thereof and DOXYL (4,4-dimethyl-1-oxazolidinyloxy) and derivatives thereof. Other examples of suitable nitroxide radicals are provided in U.S. Pat. No. 4,581,429 (Solomon et al) the contents of which are herein incorporated by reference.

The cross-linking agent used in the process of the invention preferably contains two or more double carbon-carbon bonds. Other functional groups such as hydroxyl, carboxyl, ester, amide amino, substituted amino, mercapto, silane and epoxy or the like may be present if desired. Examples of suitable cross-linking agents include divinyl benzene and derivatives of divinyl benzene and monomers containing two or more acrylate or methacrylate functional groups. Examples of such polyacrylate compounds include polyols substituted with two or more double bonds derived from acrylic or methacrylic acids. Examples of di-and tri-acrylate compounds include compounds of formula III:

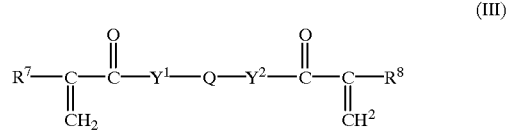

wherein $R^7$ and $R^8$ are independently selected from hydrogen, halogen $C_1$ to $C_6$ alkyl preferably methyl and substituted $C_1$ to $C_6$ alkyl such as $C_1$ to $C_6$ hydroxyalkyl;

$Y^1$ and $Y^2$ are independently selected from $NR^9$ and O where $R^9$ is independently selected from hydrogen and alkyl; and Q is a linking group which may be any linking group known in the art. Preferred linking groups include alkylene (preferably of 1 to 12 carbon atoms) a carbocyclic or heterocyclic group or polyaklylene oxide and wherein the groups may optionally be substituted with one or more substituents selected from halo, hydroxy, amino, substituted amino, silane, epoxy, acrylate or methacrylate.

Preferably Q is alkylene of 1 to 10 carbon atoms or a polyalkylene oxide and optionally include a substituent selected from hydroxy, amino silane, epoxy and acrylate or methacrylate. When one or both of $R^7$ and R8 are substituted alkyl suitable substituents include hydroxy, halo, amino, substituted amino, thiol, silane and epoxy.

Preferred polyacrylate compounds include trimethylol propane triacrylate, trimethylol propane trimethacrylate, pentaerythritol tetraacrylate, pentaaerythritol tetramethacrylate, alkylene glycol diacrylates, alkylene glycol dimethacrylates, diacrylates of polyalkylene glycols, dimethacrylates of polyalkylene glycols diacrylates of polyoxyalkyleneglycol, dimethacrylates of polyoxyalkyleneglycol, 2-cyanoethylacrylate, alkylene glycol acrylate methacrylate, polyalkyleneglycol acrylate methacrylate, polyoxyalkylene glycol acrylate methacrylate. Specific examples of cross-linking agents include divinyl benzene, ethylene glycol dimethacrylate, butanediol dimethacrylate, triethylene glycol diacrylate, 1,6-hexanediol diacrylate, trimethylolpropane triacrylate, triethylene glycol diacrylate, pentaerythritol triacrylate, 1,3-butylene glycol diacrylate and ethylene glycol acrylate methacrylate.

The choice of cross-linking agent may be used to control the architecture and chemical properties of the crosslinked network which constitutes the core of the star type microgel. Three general types of cross-linking agents may be used depending on the properties required.

When the unsaturated groups in the cross-linking monomer are equivalent their relative reactivity is determined by statical considerations. A greater degree of control is provided when the unsaturated groups have different reactivities. Without wishing to be bound by theory we believe the greater control provided by using unsaturated group of different reactivities occurs due to the occurrence of chain growth at one of the double bonds prior to completion of cross-linking. The other type of cross-linking agent which may be used includes additional functional groups which may be selected to provide the desired interaction with solvents or other species or the reactivity of the microgel. These three groups of cross-linkers will be discussed in more detail.

Examples of crosslinking agents in which the vinyl groups are equivalent include divinyl benzene and compounds of Formula III wherein $R^7$ and $R^8$ are the same and Q is unsubstituted or has symmetrical substitution. Other commercially available monomers of this type include alkylene glycol diacrylates and dimethacrylates such as butane diol diacrylate or butane diol dimethacrylate.

Examples of the second group of cross-linking agents in which the vinyl groups have distinct reactivities include compounds wherein $R^7$ and $R^8$ are different and/or $Y^1$ and $Y^2$ are different. Such cross-linking agents include with two different unsaturated groups selected from acrylate, methacrylate, acylamide and methacrylamide. The two different saturated groups may be linked for example by alkylene glycol or polyalkylene glycol linking groups. Particularly preferred cross-linking agents will distinct vinyl groups include the following:

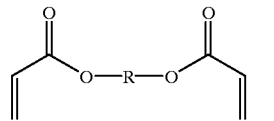

$R = (CH_2)_n$
$R = -(CH_2-CH_2-O-)_n$

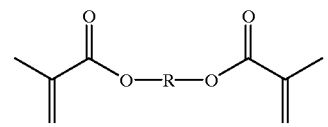

$R = (CH_2)_n$
$R = -(CH_2-CH_2-O-)_n$

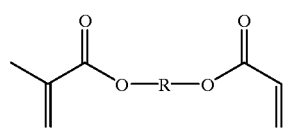

$R = (CH_2)_n$
$R = -(CH_2-CH_2-O-)_n$

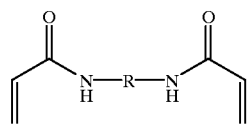

$R = (CH_2)_n$
$R = -(CH_2-CH_2-O-)_n$

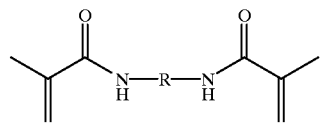

$R = (CH_2)_n$
$R = -(CH_2-CH_2-O-)_n$

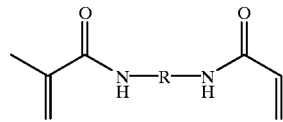

$R = (CH_2)_n$
$R = -(CH_2-CH_2-O-)_n$

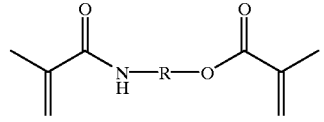

$R = (CH_2)_n$
$R = -(CH_2-CH_2-O-)_n$

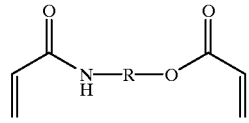

$R = (CH_2)_n$
$R = -(CH_2-CH_2-O-)_n$

-continued

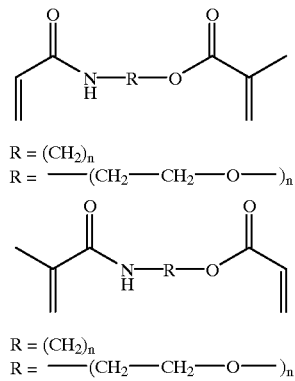

R = $(CH_2)_n$
R = ——$(CH_2$——$CH_2$——$O$——$)_n$

A third group of cross-linking agents which are useful in the invention are compounds which in addition to at least two unsaturated groups further include one or more other functional groups such as hydroxyl, mercapto, amine, halo amido and alkoxy carbonyl. Substituted compounds of this general type are particularly useful in producing star type microgels having a hydrophilic core or a core including reactive groups. Specific examples of such cross-linking agents include hydroxy substituted compounds such as pentaerythritol triacrylate and compounds of Formula III wherein Q includes one or more substituents selected from hydroxyl, amino, substituted amino, silane, epoxy acrylate, alkylene acrylate, methacrylate and alkylene methacrylate.

The invention may use mixtures of cross-linking agents. For example the use of cross-linking agents from different classes such as divinyl benzene and diacrylates or dimethacrylates may provide advantages. Further, combinations of symmetrical cross-linking agents and cross-linking agents having double bonds of different reactivities can be used to control cross-linking density.

The process of the invention may be conducted in the present of a solvent if desired. The process may, for example, be conducted in solution, in bulk or in suspension.

In preparation of star microgels the reaction is preferably conducted in a suitable solvent for the oligomer and theta-solvents are particularly preferred. We have found that in some cases the crosslinking reaction is highly efficient when a mixture of crosslinking agent and a monomer containing one unsaturated group is employed and believe the role of the monomer is to act as a spacing unit. It is also preferred that the spacing monomer solvate the arms of the star-type microgel which are derived from the oligomer.

Without wishing to be bound by theory we believe that the monomer diluent acts as a spacer monomer to control cross-linking density and to improve the efficiency of cross-linking. In some systems it may be difficult to obtain efficient cross-linking and microgel formation in the absence of a suitable monomer such as a mono-unsaturated monomer.

The spacer monomer may comprise a monomer having one or more additional functional groups to provide a means for controlling the reactivity or chemical properties of the microgel. For example, in one embodiment the spacer monomer comprises at least two types of monomers including a monomer which provides a relatively inert monomer unit and a functionalised monomer incorporating one or more additional functional groups such as hydroxyl, carboxyl, amides, amino substituted amino, thiol silane, epoxy or the like.

The spacing monomer may be the same or different from the monomer used in preparing the oligomer however in many cases it is convenient to use the same monomer. The spacer monomer is typically in the range of from 0 to 70 mole % of the polymerizable components and preferably from 5 to 70 mole %.

The process of the present invention generally has the significant advantage over prior art processes for forming microgels that it allows oligomer arms to be incorporated much more efficiently so that the proportion of unreacted residual monomer in the resulting microgel is reduced.

The microgel prepared in accordance with the process of the invention generally has a number average molecular weight of at least about $10^4$ Preferably the molecular weight is in the range of from about $10^4$ to about $10^7$ and most preferably from about $10^5$ to about $10^7$.

The microgels prepared according to the process of the invention have a range of applications.

The microgels are particularly useful as rheology control agents in solvent-borne and waterbome coatings.

In formulating coating compositions it has been necessary to compromise between providing maximum solids content and providing good durability. Whereas high solids content is best satisfied by using a low molecular weight polymer durability is best satisfied by high molecular weight. The microgels of the present invention allow the compromise to be more effectively met by providing a polymer of high molecular weight, and hence providing good durability while at the same time providing the solubility to enable a high solids content to be achieved. The microgels also allow a reduction in solvent content to be achieved without the problems of saging which recur with lower molecular weight resins.

The microgels of the invention may be used in thermo-setting or radiation curable compositions. Such compositions will generally comprise a microgel which comprises pendant functional groups which may be provided by using a monomer, alkoxyamine or cross-linking agent which has the appropriate functional group such as a hydroxy, amino, carboxyl mercapto, substituted amino, silane or epoxy group. The crosslinking agent will contain functional groups which are reactive with the pendant functional group of the microgel under the curing conditions.

The microgels of the invention may also be used in adhesives and cosmetics.

The microgels prepared according to the invention are also useful as plastic additives to improve impact resistance and to provide internal lubrication. The microgel prepared according to the invention is also useful as a pharmaceutical carrier particularly when prepared using polar functional groups which may facilitate association of the microgel with the pharmaceutical.

The invention will now be demonstrated by but it is no way limited to the following examples.

EXAMPLES

Materials

Tetramethylpiperidine-1-oxyl radical (TEMPO) and tert-butylstyrene (TBS) were obtained from Sigma Aidrich. TBS was distilled just prior to the reaction. Purification of 1,4-divinylbenzene (DVB) was carried out by the method of Wiley et al, J. Polymer Science A-1, 6, 1065 (1968). Benzene was refluxed over sodium for 16h and then distilled prior to use.

Characterization

Size exclusion chromatography (SEC) was carried out using a Waters 510 HPLC pump in conjunction with the Wyatt Technology Dawn F multi angle laser light scattering (MALLS) instrument and Waters 410 differential refractometer (DRl) on-line detectors. Wyaft Technology ASTRA and EASI software and Waters BASELINE packages were employed for data collection and analysis. A series of Waters ultrastyragel columns ($10E^3$, $10E^3$, $10E^5$ A) were used for the separation of the polymers using HPLC grade tetrahydrofuran at a flow rate of 1.0 ml/min.

Example 1 a) Preparation of 3-(4-tert-butylphenyl)-1,1-dimethyl-3-(2,2,6,6-tetramethyl pipeeridinooxy)propyl cynanide (1).

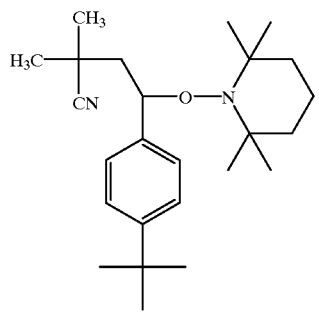
(1)

A mixture of 2,2'-azoisobutyronitrile (AIBN) (0.815 g, 4.96 mmol), TBS (0.83 g, 5.2 mmol) and TEMPO (0.382 g, 2.45 mmol) was degassed three times under freeze-thraw conditions and sealed under vacuum. The mixture was heated at 80° C. for 16 hours to afford (0.391 g, 41.6%) alkoxyamine 1 as a white crystalline solid, m.p. 109–110° C., on crystallization from diethyl ether.

| $C_{25}H_{40}N_2O$ (384.24) | Calc. | C 78, 14 | H 10, 41 | N 7, 29 |
|---|---|---|---|---|
| | Found: | C 78, 15 | H 10, 26 | N 7, 51 |

IR (Kbr): 3003 (m, Ar CH), 2969, 2938 (vs, alkyl CH), 2232 (w; CN), 1614 (w, Ar), 1466, 1363 (m, CON), 835 (m, Ar) cm$^{-1}$. MS (CI, $CH_4$: m/z 385 (M+1), 228 (M-TEMPO), 157 (TEMPO), 140 ($C_9H_{18}N$). $^1$H NMR ($CDCl_3$): δ=0.94–1.547 (m, 33H), 2.01 (dd, 1H, J=13.5, 10.8 Hz), 2.572 (dd, 1H, J=13.5, 3.3 Hz), 4.823 (dd, 1H, J=11.1, 3.3), 7.25–738 (m, 4H). $^{13}$C NMR ($CDCl_3$): δ=151.20, 138.75, 128.41, 124.87 (Ar), 124.47 (CH), 85.56 ($CH_2$—CH—O), 40.37 (CH$_3$—C—CH$_3$), 34.10 (($CH_3)_2$—C—CN)), (31.37 ((CH$_3$)$_3$C), 34.52, 30.45, 28.49, 27.33 (TEMPO CH$_3$), 20.42 ((CH$_3$)C), 17.18 ($CH_2$—CH$_2$—CH$_2$).

It was found that the molar ratio of initiator to nitroxide has a significant effect on these type of reactions and this ratio determines the proportion of product in the reaction mixture. At a high molar ratio of initiator to nitroxide, the major trapped product from the mixture was identified as the alkoxyamine 1 which incorporates a unit of TBS. This is unusual as it represents the trapping of the second formed carbon centred radical. The alkoxyamine 3 from the direct trapping of the cyanoisopropyl radical is the major product formed when a high TEMPO concentration relative to AIBN is utilized.

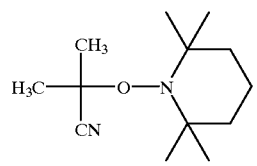
(3)

b) Preparation of Microgel.

To a feed ratio of 7:3 of TBS and DVB in benzene was added 1.6 wt % of alkoxyamine of part (a) of the Example. The resulting mixture was degassed three times under freeze-thraw conditions, sealed under vacuum and heated at 130° C. for 48 hours. Precipitation of the mixture from methanol afforded the microgel as a white solid. The co-polymer was found to be soluble in a range of organic solvents (THF, chloroform, benzene). SEC analysis of this system showed a multi-modal chromatogram with Mn ranging between $1.4 \times 10^4$–$8.0 \times 10^4$, relative to polystyrene standards. Subsequent molecular weight determination of the afforded polymer using SEC-MALLS indicated a $M_w$ ca. $10^5$, which is much higher molecular weight than indicated by polystyrene standards. These physical properties of solubility in common solvents and low intrinsic viscosity implied by SEC analysis, but high molecular weight are indicative of microgel macromolecules.

The differences between the observed molecular weights from the two techniques is attributed to the architecture of microgels. They are not statistical coil linear polymers and so their hydrodynamic volume and intrinsic viscosity will be different to that of the polystyrene standards employed in SEC. MALLS is a means of absolute molecular weight determination, and consequently is not reliant on standards or affected by variance in architecture. Also, it should be noted that the light scattering signal is proportional to molecular weight, hence higher molecular weights afford a larger light scattering response. Consequently, the multimodual distribution observed via the DRl detector is not as obvious using MALLS> Also, the multimodal nature of the sample is consistent with reported free radically derived microgels.

This successful application of the living free radical technique to the synthesis of "one-pot" microgels establishes the ability to synthesize these systems in a controlled manner by radical methodology.

Example 2 a) Preparation of Aminoxy Terminated Poly(tert-Butylstyrene) (2) Derived from Alkoxyamine (1).

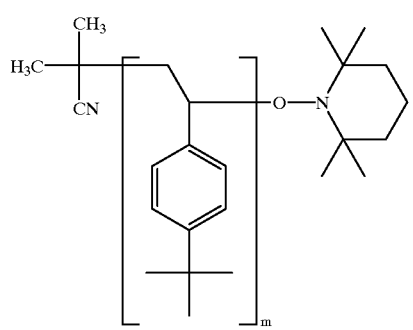
(2)

TBS and the alkoxyamine (1) prepared by the method of Example 1a were dissolved in benzene, degassed 3 times under freeze-thraw conditions and sealed under vacuum. The mixture was heated at 130° C. for the desired time to afford poly(tert-butylstyrene) of narrow polydisperity as a white solid after precipitation from methanol.

b) Preparation of Microgel.

Using similar conditions to that described above for microgel generation, aminoxy terminated poly (TBS) 2 was heated at 130° C. in the presence of TBS and DVB in benzene to afford a white powder on precipitation from methanol. This copolymer demonstrated similar solubility and multi-modal SEC to the microgel derived from 1. Again, the characteristic higher molecular weight was evident from the SEC-MALLS analysis, displaying a molecular weight in the order of $10^5$ being considerably higher than that determined with respect to polystyrene standards.

The synthesis of the microgels is the first report of a living free radical technique being applied to the preparation of crosslinked polymeric networks. The ability to use this technique in these systems provides control previously not available and broadens the range of monomers which can be incorporated into star branched systems currently limited by the problems associated with anionic polymerization.

Example 3

The procedure of Example 1 was repeated using the mixture of cross-linking agent and tert-butylstyrene in the proportions listed in Table 1.

The reaction time used and the resulting GPC and MALLS results are also shown in Table 1.

Example of Microgels Prepared by Copolymerization of Divinyl and Monovinyl Monomers Using Alkoxyamine (1)

TABLE 1

| Crosslinking agent: TBS | Reaction time (Hour) | GPC Results $M_w$ | MALLS Results $M_w$ |
|---|---|---|---|
| DVB:TBS (30:70) | 24 | $4.17 \times 10^4$ | $2.13 \times 10^5$ |
|  | 48 | $5.99 \times 10^4$ | $4.75 \times 10^5$ |
|  | 72 | $7.18 \times 10^4$ | $7.60 \times 10^5$ |
| BDDMA:TBS (30:70) | 71 | $5.32 \times 10^4$ | $1.39 \times 10^5$ |
| EGDMA:TBS (30:70) | 71 | $2.69 \times 10^4$ | $4.13 \times 10^4$ |
| BDDA:TBS (30:70) | 19 | $1.66 \times 10^5$ | $2.13 \times 10^6$ |
| BDAM:TBS (20:80) | 48 | $2.28 \times 10^4$ | $5.26 \times 10^4$ |

TBS = t-butylstyrene
DVB = 1,14-divinylbenzene
BDDMA = 1,4-butanediol dimethacrylate
EGDMA = 1,2-Ethylene glycol dimethacrylate
BDDA = 1,4-butanediol diacrylate
BDAM = 1,4-butanediol acrylate methacrylate

Example 4

The procedure of Example 2 was repeated using divinyl monomers and tert-butyl styrene on a 30:70 molar ratio. Details of the microgel obtained are provided in Table 2 below.

Example of Microgels Prepared by Copolymerization of Divinyl and Monovinyl Monomers Using Polymeric Alkoxyamine (2)

Polymeric alkoxyamine: $M_n$=2710 Polydipersity=1.09

TABLE 2

| Feed Ratio (dvb:tbs) | Reaction time (Hour) | GPC Results $M_w$ | MALLS Results $M_w$ |
|---|---|---|---|
| 30:70 | 24 | $1.52 \times 10^4$ | $8.75 \times 10^4$ |
|  | 48 | $2.21 \times 10^4$ | $2.08 \times 10^5$ |
|  | 72 | $3.11 \times 10^4$ | $2.33 \times 10^5$ |
| EGDMA:TBS 30:70 | 48 | $1.96 \times 10^4$ | $2.72 \times 10^4$ |
| BDDMA:TBS 30:70 | 48 | $2.21 \times 10^4$ | $2.95 \times 10^4$ |

Example 5

This Example demonstrates the preparation of a microgel from an oligomer which is a block copolymer including a monomer with an additional functional group.
Polystyrene-block-poly(4-vinylpyridine)

This example demonstrates the preparation of an alkoxyamine containing an oligomer which is a block copolymer.

4-vinylpyridine (0.909 g, 8.65 mmol) and polystyrene-TEMPO adduct ($M_n$=3555, $M_w/M_n$=1.10) (0.1 g) were placed into a decomposition flask and degassed via several freeze-thaw cycles. The reaction mixture was heated for varied times at 130° C., and the polymer recovered as a precipitate from a large excess of water, purified by reprecipitation into water from methanol, and dried thoroughly. The molecular weights were determined by GPC. Refer to Table 4 for reaction times and results.

TABLE 4

Reaction times and results for block copolymerizations in bulk

| Sample | Reaction time (hr.) | Yield (g) | Conversion (%) | $M_n$ | $M_w/M_n$ |
|---|---|---|---|---|---|
| 1 | 5 | 0.179 | 8.7 | 3732 | 1.27 |
| 2 | 10 | 0.242 | 15.6 | 4780 | 1.38 |
| 3 | 15 | 0.374 | 30.1 | 4456 | 1.53 |

The above prepared alkoxyamine may be used to prepare a microgel by the method of Example 2(b).

Example 5

The procedure of Example 2 was repeated using divinyl benzene and styrene. Details of microgel obtained are provided on Table 3.

Polymeric alkoxyamine $M_n$=9063 $M_w/M_n$=1.13

TABLE 3

| PS-TEMPO (g) | STYRENE (g) | YIELD (g) |
|---|---|---|
| 0.5 | — | 0.5252 |
| 0.4 | 0.1 | 0.4607 |
| 0.3 | 0.2 | 0.4023 |

What is claimed is:

1. A process for preparation of a microgel comprising reacting an alkoxyamine derived from a tertiary nitroxide free radical with an unsaturated monomer composition comprising a cross-linking agent comprising at least two double bonds and optionally one or more further monomers selected from monounsaturated monomers and conjugated diene monomers.

2. A process according to claim 1 wherein the alkoxyamine is of Formula I

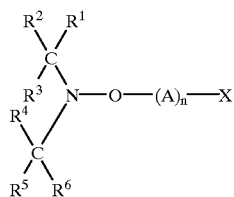
(I)

wherein $R^1$, $R^2$, $R^5$ and $R^6$ are independently selected from the group consisting of straight chain or branched substituted or unsubstituted alkyl groups of a chain length sufficient to provide steric hindrance and weakening of the O—$(A)_n$X bond;

$R^3$ and $R^4$ are independently selected from straight chain or branched chain alkyl or substituted alkyl groups or $R^3$CNCR$^4$ may be part of a cyclic structure which may be fused within another saturated or aromatic ring substituent;

A is a monomeric unit which when there is more than one A may the same or different;

n is zero or greater than zero; and

X is an initiator fragment.

3. A process according to claim 2 wherein n is less than 5 and said monomer composition comprises said one or more further monomers selected from mono-unsaturated monomers and conjugated diene monomers and wherein the composition optionally further comprises a nitroxide radical in addition to the alkoxyamine.

4. A process according to claim 2 wherein n is at least 5.

5. A process according to claim 2 wherein in the alkoxy amine the radical $(A)_n$X is an oligomer radical having molecular weight of from 1000 to 15,000.

6. A process according to claim 1 wherein the cross-linking agent is selected from the group consisting of divinyl benzene, derivatives of divinyl benzene and compounds of Formula III:

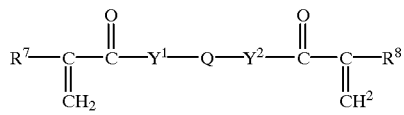
(III)

wherein $R^7$ and $R^8$ are independently selected from the group consisting of hydrogen, $C_1$ to $C_6$ alkyl and $C_1$ to $C_6$ hydroxyalkyl; $Y^1$ and $Y^2$ are independently selected from NR$^9$ and O wherein $R^9$ is independently selected from hydrogen and alkyl; and Q is a linking group optionally substituted with one or more substituents selected from the group consisting of hydroxy, amino, substituted amino, epoxy, silane, acrylate, alkylene acrylate, methacrylate and alkylene methacrylate.

7. A process according to claim 6 wherein the cross-linking agent is of Formula III and wherein in at least one of the pairs of substituent $R^7$, $R^8$ and $Y^1$, $Y^2$ one of the substituents of the pair is different from the other substituent of said pair.

8. A process according to claim 1 wherein the cross-linking agent comprises two different unsaturated groups selected from the group consisting of acrylate, methacrylate, acrylamide and methacrylamide.

9. A process according to claim 1 wherein the cross-linking agent is present in an amount of from 5 to 60 mole percent based on the total of polymerizable components.

10. A process according to claim 3 wherein the alkoxyamine is present in an amount of at least 5 mole % and the further monomer is present in an amount of up to 80 mole % based on the total number of moles of polymerizable composition.

11. A process according to claim 4 wherein the alkoxyamine is present in an amount of from 50 to 95% of the total polymerizable component and the monomer composition optionally comprises up to 45% of the further monomer selected from mono-unsaturated monomers and conjugated diene monomers.

12. A process according to claim 2 wherein n is 1 or more and the monomer units (A) are derived from one or more monomers selected from the group consisting of alkenes, acrylates, methacrylates, styrene or styrenic monomers and acrylonitrile or substituted acrylnitrile, conjugated dienes wherein the monomers may optionally be substituted with one or more functional groups selected from halo, hydroxy, amino, carboxyl, mercapto, substitute amino, silane and epoxy.

13. A process according to claim 4 wherein the oligomer $(A)_n$ is a block or statestical copolymer and at least one of said monomer units has a polar functional group.

14. A process according to claim 1 wherein the microgel has a molecular weight of at least $10^4$.

15. A microgel when prepared by the process of claim 1.

16. A plastics or coating composition comprising a microgel prepared according to the process of claim 1.

17. A pharmaceutical composition comprising a microgel prepared according to claim 1 and a pharmaceutically active compound associated with the microgel.

18. A thermosettable composition comprising:
  (a) a microgel prepared according to the process of claim 4 wherein at least one component selected from the one or more of the monomer unit A, the cross-linking agent and the further monomer comprise a functional group providing pendant functional groups on said microgel; and
  (b) a cross-linking agent containing at least two functional groups adapted to react with the pendant functional groups on said microgel to provide curing of the thermosettable composition.

19. A process according to claim 10 wherein the further monomer is present in an amount from 10 to 80% based on the total number of moles of polymerizable composition.

* * * * *